US011806963B2

(12) United States Patent
Britton et al.

(10) Patent No.: US 11,806,963 B2
(45) Date of Patent: Nov. 7, 2023

(54) HAND-OPERATED SCREW PRESS

(71) Applicants: Benjamin Britton, Conifer, CO (US); Kyle Manuel, Arvada, CO (US)

(72) Inventors: Benjamin Britton, Conifer, CO (US); Kyle Manuel, Arvada, CO (US)

(*) Notice: Subject to any disclaimer, the term of this patent is extended or adjusted under 35 U.S.C. 154(b) by 711 days.

(21) Appl. No.: 16/830,137

(22) Filed: Mar. 25, 2020

(65) Prior Publication Data
US 2021/0299989 A1 Sep. 30, 2021

(51) Int. Cl.
| | | |
|---|---|---|
| *B30B 15/34* | (2006.01) | |
| *B30B 15/06* | (2006.01) | |
| *B30B 1/20* | (2006.01) | |
| *B30B 15/00* | (2006.01) | |
| *B30B 9/06* | (2006.01) | |

(52) U.S. Cl.
CPC ............... *B30B 15/34* (2013.01); *B30B 1/20* (2013.01); *B30B 15/0094* (2013.01); *B30B 15/064* (2013.01); *A61K 2236/31* (2013.01); *A61K 2236/37* (2013.01); *B30B 9/06* (2013.01)

(58) Field of Classification Search
CPC .. B30B 1/18; B30B 1/20; B30B 15/14; B30B 15/34; B30B 15/064; B30B 15/281; B30B 9/60; B30B 15/04; B30B 15/0058; B30B 15/047; B30B 9/06; B30B 15/0094; A61K 2236/31; A61K 2236/37
See application file for complete search history.

(56) References Cited

U.S. PATENT DOCUMENTS

| | | | | |
|---|---|---|---|---|
| 1,245,235 | A  * | 11/1917 | Jarecki ...................... | B30B 1/18 100/289 |
| 1,825,686 | A  * | 10/1931 | Walker ...................... | B30B 1/18 192/84.1 |
| 2002/0025358 | A1 * | 2/2002 | Nelson .................... | B29C 43/50 425/422 |
| 2011/0076079 | A1 * | 3/2011 | Robinson .............. | B41F 17/003 100/295 |
| 2016/0250816 | A1 * | 9/2016 | Robinson ............ | B30B 15/0029 100/35 |
| 2018/0178473 | A1 * | 6/2018 | Perez ........................ | B30B 9/06 |
| 2018/0340133 | A1 * | 11/2018 | Carbone ................... | C11B 1/06 |
| 2019/0184667 | A1 * | 6/2019 | Cao ........................... | B30B 1/04 |
| 2019/0263079 | A1 * | 8/2019 | Britton .................... | B30B 15/34 |
| 2020/0147915 | A1 * | 5/2020 | Mayer ................... | B30B 15/064 |

FOREIGN PATENT DOCUMENTS

WO  WO-2019056779 A1 *  3/2019 ............... B30B 1/00

\* cited by examiner

*Primary Examiner* — Jimmy T Nguyen
(74) *Attorney, Agent, or Firm* — BURNS & LEVINSON LLP; Daniel McGrath

(57) ABSTRACT

A hand-operated screw press for users to press cannabis flower or isolated trichome heads without an air compressor, hydraulic unit or solvents used in the process. A digital load cell is provided, as is a full color LCD touch screen display for showing and recording force in real time. A mechanism for detecting the end point of a process is also provided. A recipe representative of heat plate temperature, time of operation, pressure ramping, capacity of the screw press, type of raw material, or mass of raw material can be created and stored for use on any suitable rosin press machine.

14 Claims, 8 Drawing Sheets

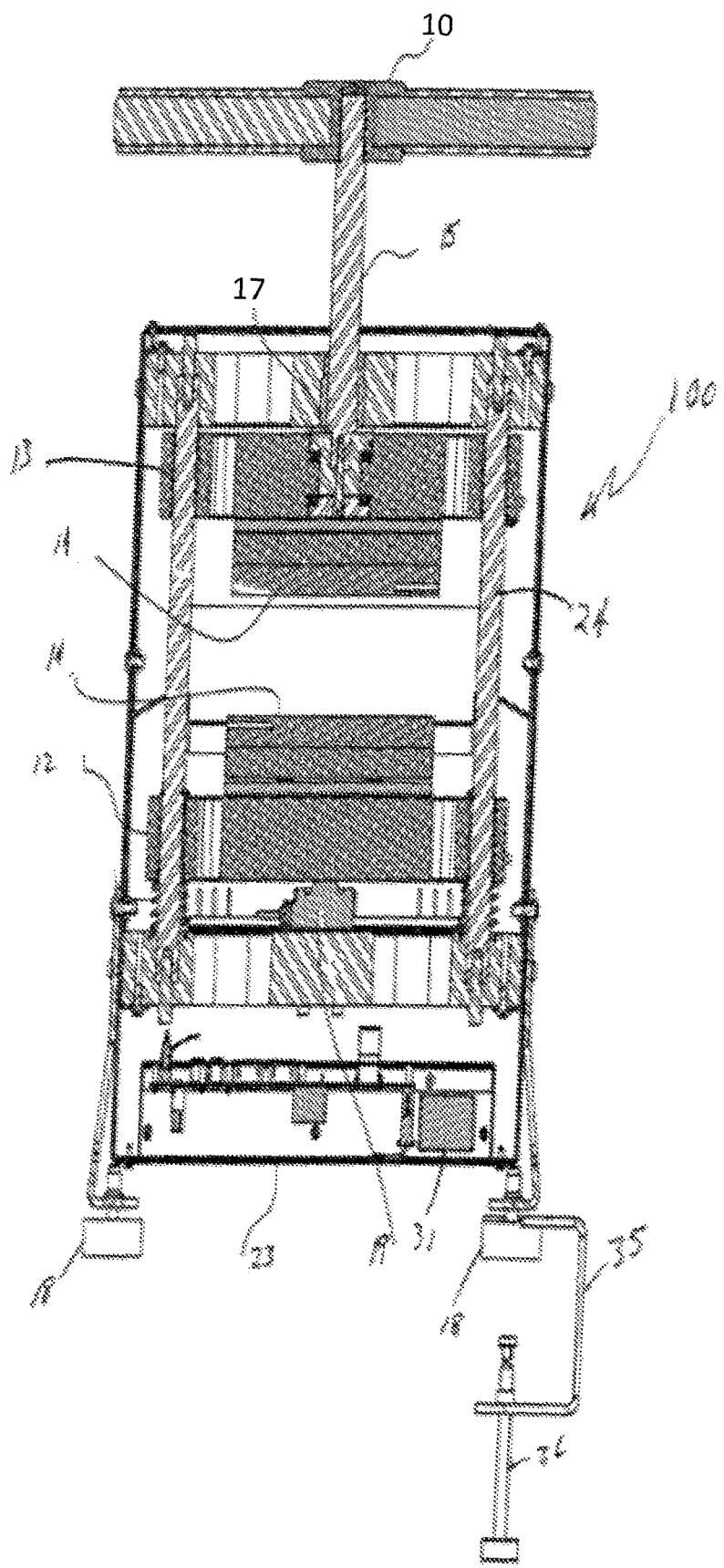

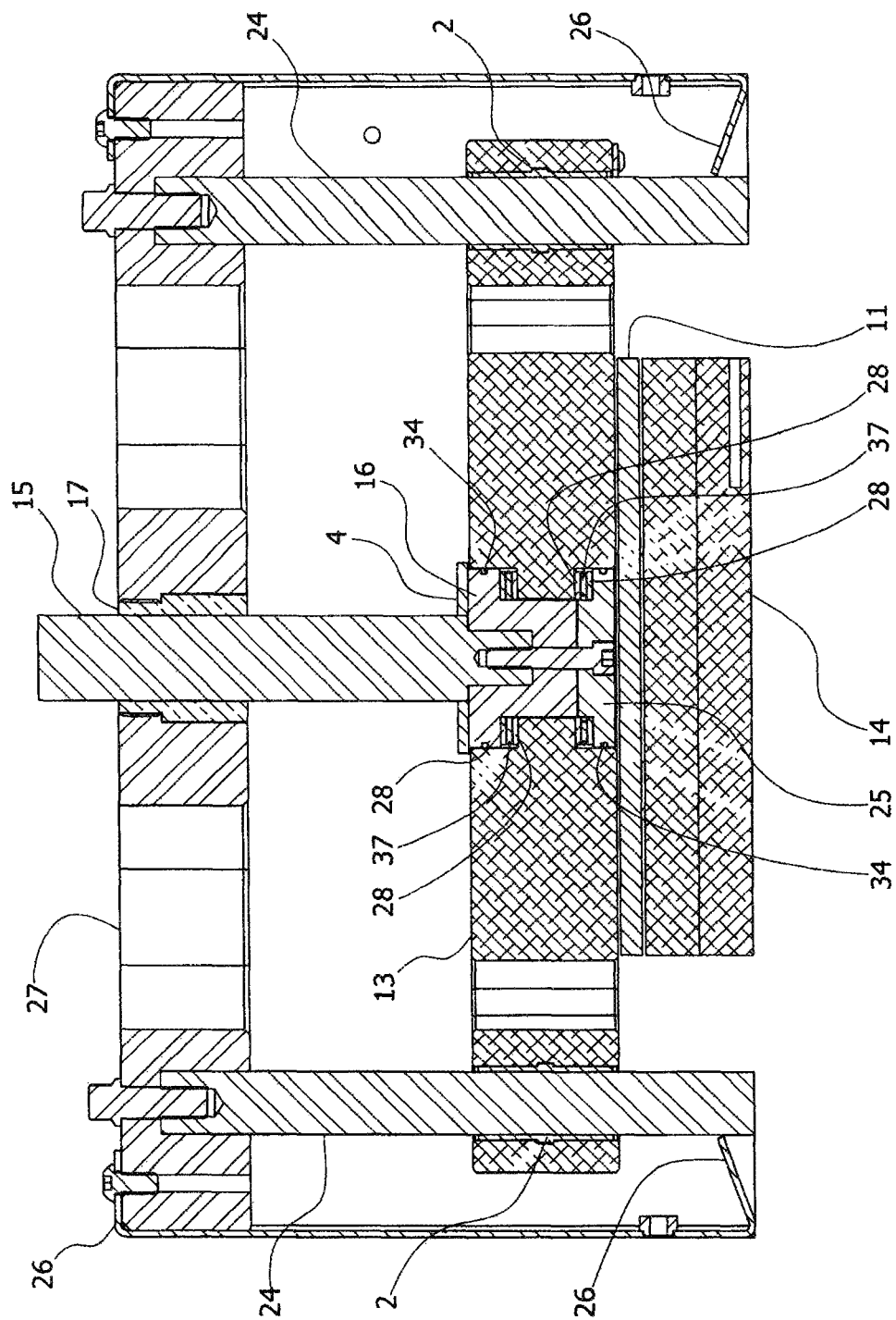

HAND-OPERATED SCREW PRESS

RELATED PATENT APPLICATION

The present invention is related to U.S. provisional patent application No. 62/823,498 for HAND-OPERATED SCREW PRESS, filed Mar. 25, 2019, and claims the priority date thereof.

FIELD OF THE INVENTION

The present invention pertains to presses for pressing cannabinoids and, more particularly, to a hand-operated screw press.

BACKGROUND OF THE INVENTION

Presses have been used for extracting liquid from plant material to create concentrates for many years and are especially useful in solventless operations. Solvent-free products are often regarded as the superior product for medical and palliative purposes due to their purity to the plant. Unlike other concentrated products, a solvent-free product contains only what came from the plant. In doing so, this eliminates any risk of other compounds or chemicals interfering with a patient's treatment.

Cannabis extraction equipment now allows producers to create solventless products for patients in an array of consumption methods. Today, solventless extraction equipment includes enhanced rosin technology and extends to vaporizer products, topicals, and edibles as well.

Often, presses used by industrial companies are motorized for efficient extraction. In the field of cannabinoids, home growers and amateur rosin pressers have no need for such industrial products, nor do they need such capacity or throughput. A manually operated press allows users to make concentrates with ease at home or anywhere and is therefore, a better alternative for such users to those industrial machines. Moreover, laboratories and production facilities often need a small batch solution to trial run a specific lot to verify yields before committing to processing the rest of the lot. A manually operated press is an affordable tool to run small batch tests while not interfering with production equipment.

Hand-operated presses, however, generally do not include ways for measuring the force applied to the plant in the course of operation. Nor do such hand-operated presses have built-in indicators or alarms to indicate when a pressing force exceeds a predetermined value.

The inventive screw press incorporates a lead screw that allows for precision in the rosin pressing process. A user can increase pressure by as little as 10-15 lb/f at a time. When pressing high quality materials in small batches, that level of control is vital to ensure the best quality concentrates possible. Moreover, the inventive screw press includes a load cell for measuring the three applied to the materials being processed. The inventive screw press also has an alarm to indicate when a pressing force exceeds a predetermined value. The press also includes pre-set recipes that guide the user through the production process. Interactive graphics show the user whether force must be adjusted, by how much, and in which direction. To control and monitor the press, a touch screen is provided.

DESCRIPTION OF RELATED ART

U.S. Pat. No. 10,005,252 issued to Kanzler, et al. on Jun. 16, 2018 for SCREW PRESS describes a screw press comprising a shaft and a spiral helix, wherein the helix goes over in the inlet region of the screw press into a freely projecting helix. A tube is provided in the inlet region of the screw press. As a result, on the one hand the screen area can be increased greatly in size, but on the other hand the co-rotation of the suspension with the shaft can be reduced or avoided.

U.S. Pat. No. 7,461,591 issued to Babbini on Dec. 9, 2008 for SCREW PRESS FOR SQUEEZING OUT FIBROUS MATERIAL describes a screw press for pressing fibrous material (in particular sugar beet pulp) having a pair of adjacent counter-rotating shafts parallel axes. The shafts each have a helical structure that winds in the opposite direction to the helical structure of the other shaft and a perforated filtering cage enclosing said helical structures. A loading hopper feeds the fibrous material to the press with a discharge aperture for the exit of the pressed material. The helical structures have a helix and a helical element, which has at least one perforated surface and a helical interspace with the outer surface of the shaft. The perforated surface has a length along the axis of the shaft which is less than the pitch of the helix so as to receive the helix of the adjacent shaft.

U.S. Pat. No. 5,379,688 issued to Ishii on Jan. 10, 1995 for METHOD OF AND APPARATUS FOR AUTOMATICALLY CONTROLLING PRESSING FORCE OF PRESS MACHINE describes controlling pressing force with which a die tool presses on a workpiece to be constant at all times. The magnitude of pressing force with which the die tool presses on the workpiece during press operation is detected with a semiconductor strain gauge, and the pressing force detected, and a preset pressing force are compared with each other by a controller. If there is a difference between the pressing force detected and the preset pressing force, a screw rod is turned by an AC servomotor so as to adjust the length of a lower ram, thereby controlling the pressing force.

U.S. Pat. No. 7,794,597 issued to Campbell on Sep. 14, 2010 for TREATMENT OF WASTE MIXTURE CONTAINING LIQUIDS AND SOLIDS describes a facility for treating solid and liquid waste that includes a receiving station, a screening station, a preprocessing station, a press station and a processing station. The screening station is connected to an inlet capable of receiving liquid and solid waste and includes a screen for capturing at least some of the solid waste. The preprocessing station is in fluid communication with the screening station and includes a degrit chamber for settling out an additional amount of the solids. The press station included at least one alkali mixing tank and a screw press for separating out an additional portion of the solids. The processing station includes at least one aerobic microorganism generating unit for converting nitrites into nitrogen gas and consuming carbon-based waste material.

U.S. Pat. No. 4,286,512 issued to Berggren on Sep. 1, 1981 for SCREW-PRESS describes a screw press for pressing liquid from fibrous slurries, such as paper pulp, sludge, sedimentation and like material, in which the material is fed into the press at one end of a press screw arranged within a cylindrical strainer drum and rotatable about its longitudinal axis, and fed out of the press through a discharge zone located at the other end of said screw. The core of the screw has a successively increasing diameter along the major part of its length such that the space defined between the core and the wall of the drum gradually decreases in the feed direction. The drum is arranged to rotate at a speed which differs from the speed of rotation of the screw. The speed of rotation of the drum is so precise that the drum obtains, as the result of the centrifugal force, an effective draining of the free liquid present in the slurry and the liquid pressed from said slurry due to the action of the press-screw. Preferably, the press is provided with means for introducing washing liquid in at least one stage for the purpose of washing material introduced into the press.

None of the aforementioned patents include a hand-operated screw press for users to press cannabis flower or isolated trichome heads without an air compressor, hydraulic unit or solvents used in the process. Moreover, none of these references discloses a digital load cell and display for showing force readout in real time. Nor is a full color LCD touch screen with custom software disclosed.

SUMMARY OF THE INVENTION

In accordance with the present invention, there is provided a hand-operated screw press with heat plates, capable of exerting up to approximately 1,000 psi of pressure across the material in the preferred embodiment. The pressure control mechanism allows for as little as 10 lb force increments. Heat from 0° F.-approximately 300° F., with less than 1-degree Fahrenheit accuracy, is evenly distributed. No air compressor or hydraulic unit is required, nor are solvents used in the process. An accurate force measuring, fully calibrated, digital load cell displays bag pressure in real time. A full color LCD touch screen is provided with custom software so a user can save up to 29 pre-set recipes that can be repeated for consistent results. The LCD touch screen allows a user to see exactly how much pressure is being applied in order to follow recipes and recreate strain-specific parameters for consistent concentrates, the recipe being scalable depending on screw press capacity and usable on any suitable rosin press.

BRIEF DESCRIPTION OF THE DRAWING

A complete understanding of the present invention may be obtained by reference to the accompanying drawing, when considered in conjunction with the subsequent detailed description, in which:

FIG. 5 is another plan cross sectional view of the front of screw press;

FIG. 7 is a plan cross sectional front detail view of the upper half of the screw press.

Like reference numerals refer to like parts throughout the several views of the drawings.

DETAILED DESCRIPTION OF THE PREFERRED EMBODIMENT

Although the following detailed description contains specific details for the purposes of illustration, those of ordinary skill in the art will appreciate that variations and alterations to the following details are within the scope of the invention. Accordingly, the exemplary embodiments of the invention described below are set forth without any loss of generality to, and without imposing limitations upon, the claimed invention.

A hand-operated screw press is provided for users to press cannabis flower or isolated trichome heads without an air compressor, hydraulic unit or solvent used in the process. A digital load cell is provided, as is a full color LCD touch screen display for showing force readout in real time.

Figure 1:
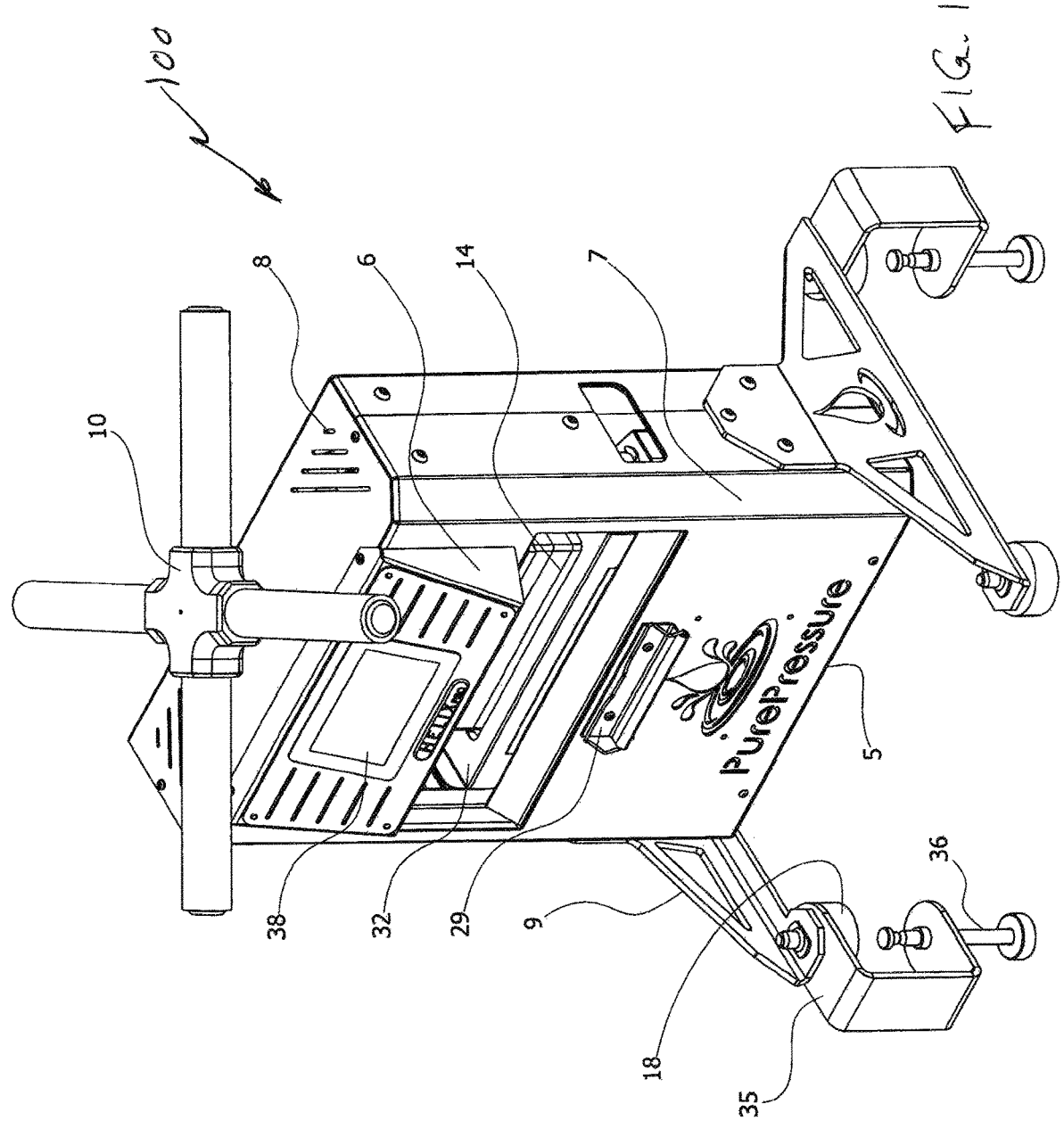
FIG. 1 is a perspective view of a screw press in accordance with the present invention.

Referring now to FIG. 1, there is shown a perspective view of a screw press 100 in accordance with the present invention. An X-shaped, removable, magnetic handle 10 is rotatably mounted to, and forms a part of, screw press 100. It should be understood that other suitably shaped handles (e.g., circular, hexagonal, etc.) can be used without departing from the scope of the invention. Front and housing enclosure 7 of screw press 100 has a display housing 6 mounted thereto. Within display housing 6 in the preferred embodiment is a full color, digital LCD touch screen display 38, such as manufactured by Riverdi Company as Model No. RB-Riv-04RVT43ULFNWC01. Other types of displays (e.g., LED, OLED, etc.) can be used to perform the same functions as digital LCD display 38 without departing from the scope of the invention.

Upper and lower heat platens 14 are disposed below display housing 6. Heat platens 14 are capable of being heated from 0° F.-approximately 300° F., the heat being evenly distributed in operation.

A removable collector tray or drip pan 32 is disposed beneath and surrounding heat platens 14, a parchment clip 29 is mounted to the front enclosure 7 of screw press 100, and a removable electrical enclosure box 5 contains electronic components, described hereinbelow.

Supporting screw press 100 are vertical legs 9, to which are attached leveling feet 18, well known in the art. Connected to leveling feet 18 or vertical legs 9 are C-clamp table clamps 35, to which are attached table clamp hand screws 36. Other support and leveling mechanisms may be used to provide support and leveling functions without departing from the scope of the invention. A hinging mechanism may be placed between the press and the vertical legs allowing the press to rotate to a desired angle and lock in place. Doing so allows the user to easily load the material (not shown) with press 100 oriented vertically, then to apply the initial pressing force, rotate press to the desired angle to promote the gravitational flow of rosin and continue through the remainder of the recipe prior to returning to the vertical position.

Often it is more cost effective to dial in a recipe on a small batch before scaling up to a production sized batch. Utilizing helix press 100, a user may create the perfect recipe for a given raw material. Once that recipe has been created, firmware can properly scale the recipe up in size. That scaled recipe can be transferred to another press 100 of any size. Often, a recipe is created on a helix press 100 and then run on a Longs Peak press, not shown.

Recipe scaling is performed by calculating the pressure (force/area) at a filter bag, not shown, and then scaling up the bag size while maintaining the original pressures. As area increases (larger bag footprint) the force must also increase to keep pressure constant. There are limitations to the maximum force that can be exerted by each machine. If the recipe cannot be scaled within machine limitations, the firmware adjusts the recipe and notifies the user. The user merely instructs the firmware as to which recipe to scale as well as the size to which the recipe is to scale. The new recipe is displayed on display 38 and can be entered as a new recipe on any suitable rosin press, such as those manufactured by the present assignee.

Figure 2:
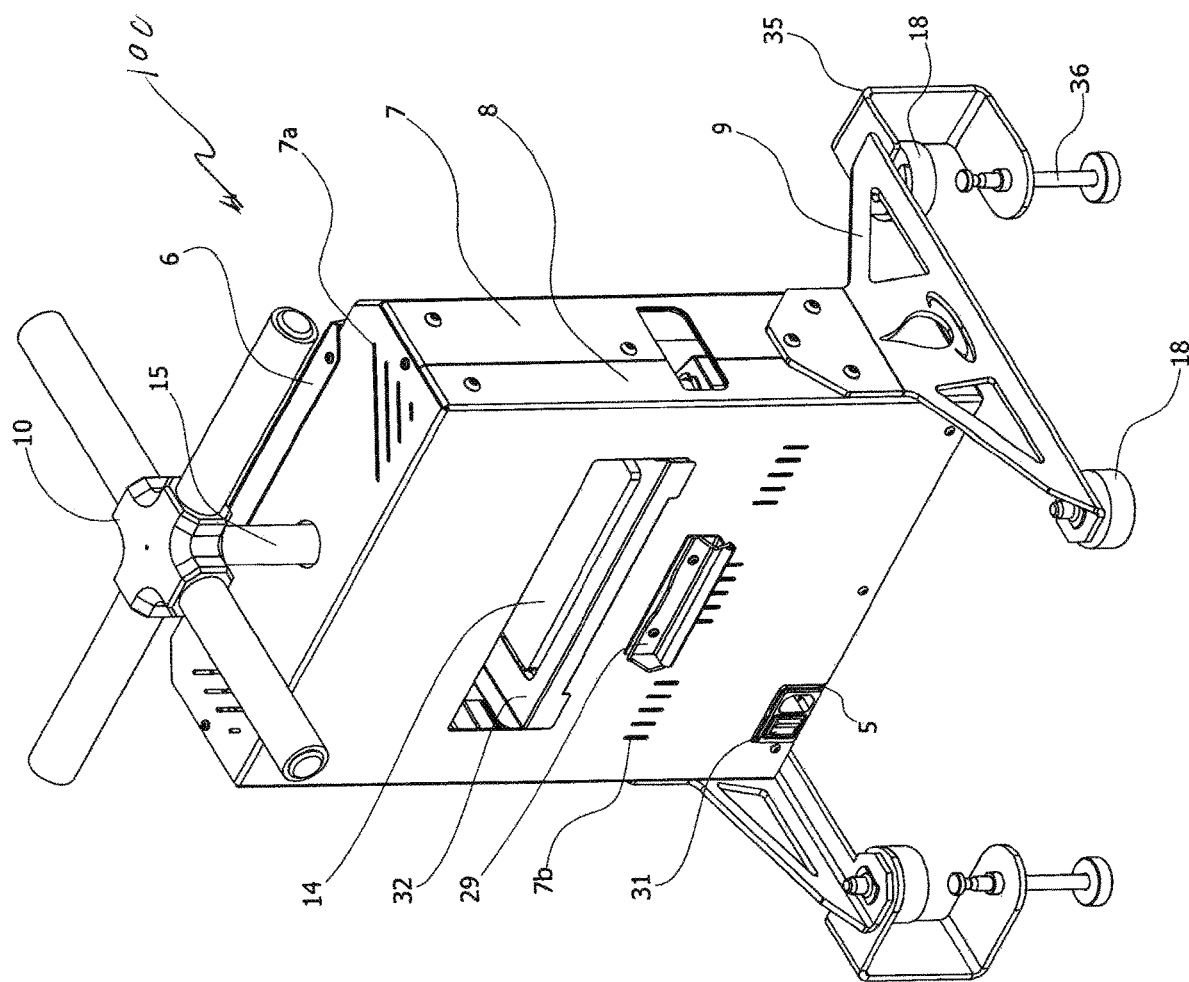
FIG. 2 is a perspective view of the rear side of the screw press shown in FIG. 1.

Referring now to FIG. 2, there is shown a perspective view of the rear side of the inventive screw press 100 shown in FIG. 1. Handle 10 is rotatably mounted to a shaft of a lead screw 15. Front and rear housing enclosures 7 and 8 have slots 7a, 7b, respectively, for providing natural heat ventilation.

A power entry module 31 is disposed at the lowermost part of rear housing enclosure 8, as shown.

Figure 3:
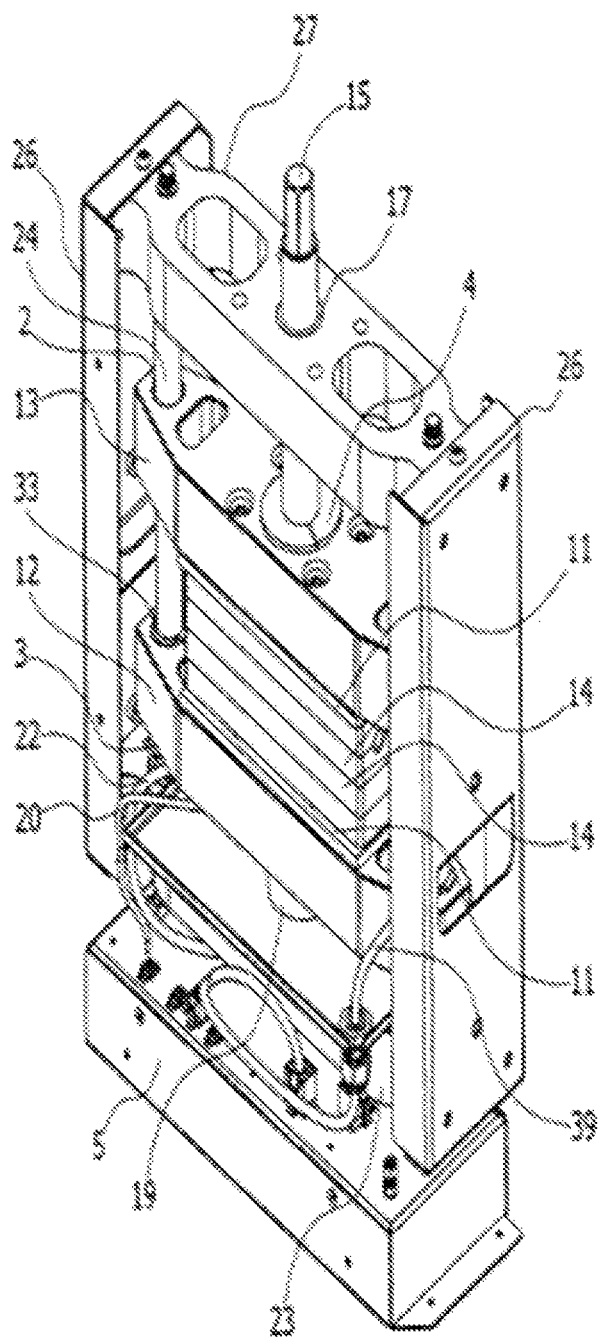
FIG. 3 is a front perspective view of the screw press with the sheet metal cover removed.

Referring now to FIG. 3, there is shown a front perspective view of screw press 100 with the sheet metal covers 7 and 8 removed. A top structural main frame member 27 is contoured to accept lead screw 15 and a lead screw nut 17. Surrounding lead screw 15 and resting on upper heat plate truss 13 is a cushioning washer 4.

Top structural main frame member 27 is attached at both ends to main frame side handles 26. Supporting both ends of top structural main frame member 27 are main frame guide rods 24 that extend through upper heat plate truss 13 and lower heat plate truss 12 down to a lower structural frame member 23. Bottom structural main frame member 23 forms the base of screw press 100, as shown. Heat plate insulation 11 surrounds heat platens 14. Composite linear slides 2 are provided to facilitate the low friction gliding of heat plate trusses 12, 13 along guide rods 24. Likewise, a retaining ring 33 surrounds guide rods 24 holding the lower truss 12 in place. In addition, guide rods 24 resist the rotary forces from twisting handle 10 and translate the force into linear movement via screw 15 and nut 17. The diametral clearance of guide rods 24 within composite linear slide 2 is 0.0003" on upper heat plate truss 13, resulting in a rigid upper assembly that improves the life of a flat needle bearing 37. The diametral clearance of guide rods 24 within composite linear slide 2 is 0.0013" on lower heat plate truss 13, resulting in a lower assembly that has multiple degrees of freedom, ensuring proper contact between heat platens 14 and the material being pressed. A load cell 19 acts as the center pivoting point for lower heat plate truss 12. This is a different approach to the same mechanism described in pending patent application Ser. No. 15/904,164, filed Feb. 23, 2018, for
Heated Press Utilizing a Pivoting Actuating Truss for Extraction of Oils.

Disposed beneath lower heat plate truss 12, on either side thereof, is a pair of compression springs 3 which pushes upwardly and lifts lower heat plate truss 12 off of load cell 19 and up against C-clips 33 when force is removed. This allows load cell 19 to return to zero every run, ensuring a repeatable process. Additionally, springs 3 allow the user to apply less than 15 lbs of force during a preheat process which begins to melt the natural oils in the raw material before applying substantial pressure in order to prevent a blowout. The small force also helps to pin material and prevent slippage early in the pressing cycle.

A lower heater wire harness 22 is disposed beneath lower heat plate truss 12, as is a load cell wire harness 20 electrically connected to load cell 19, and an upper heater wire harness 39. All of these electrical components are contained in and protected by removable electrical enclosure box 5.

Figure 4:
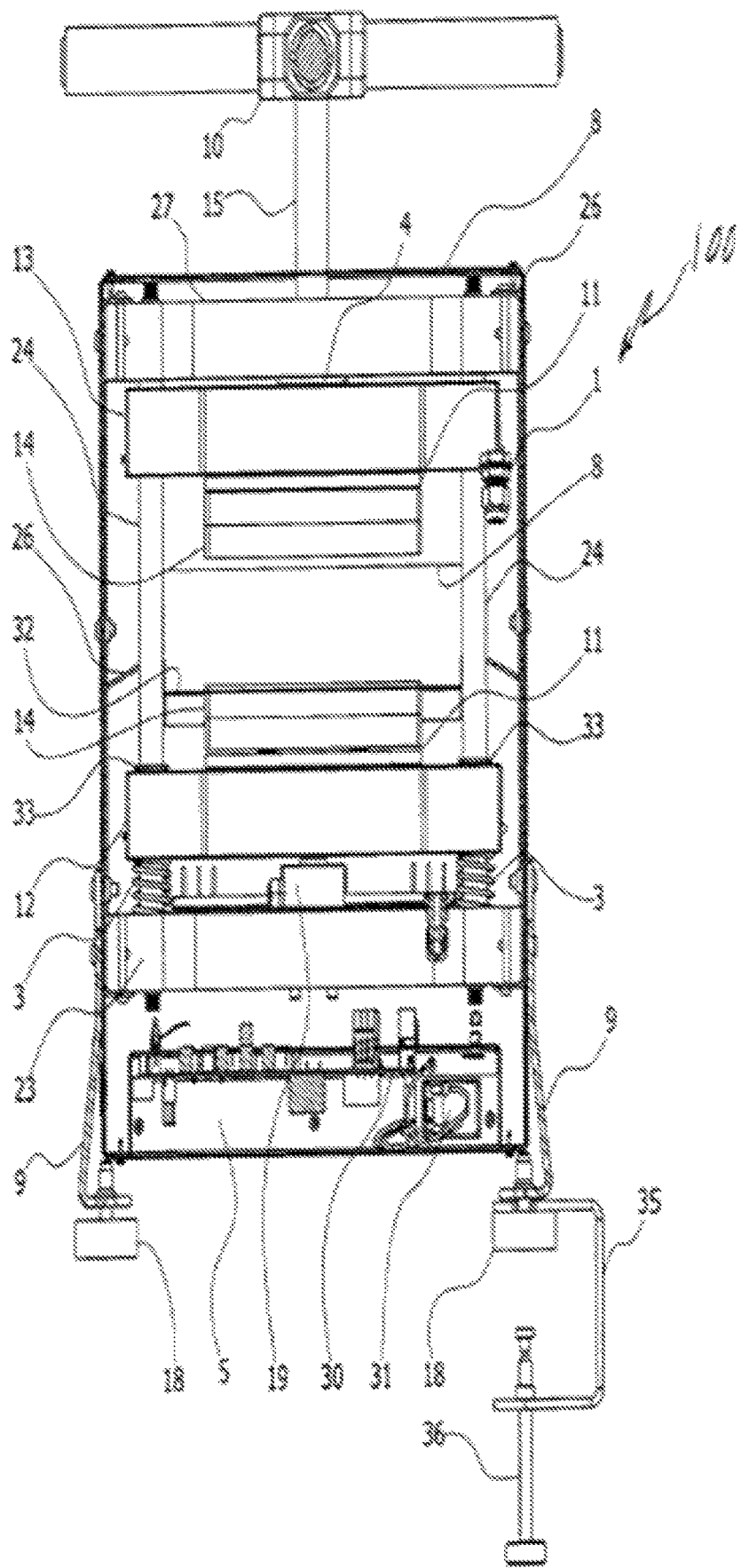
FIG. 4 is a plan cross sectional view of the front of screw press.

Referring now to FIG. 4, there is shown a plan cross sectional view of the front of screw press 100. A cable gland mount 1 is disposed beneath the lower surface of upper plate truss 13. Load cell 19 is disposed proximate the lower surface of lower heat plate truss 12 to measure the downward force thereof during screw press operation.

A circuit board 30 forms part of the electrical components housed in removable electrical enclosure box 5. Connected to circuit board 30 are electrical components (not shown) that control the force readout of load cell 19 on display 38, as well as set a force value, above which the readout of load cell 19 triggers an alarm, and memory for storing recipes of temperature, pressure ramping, and time.

Referring now to FIG. 5, there is shown another plan cross sectional view of the front of screw press 100.

Figure 6B:
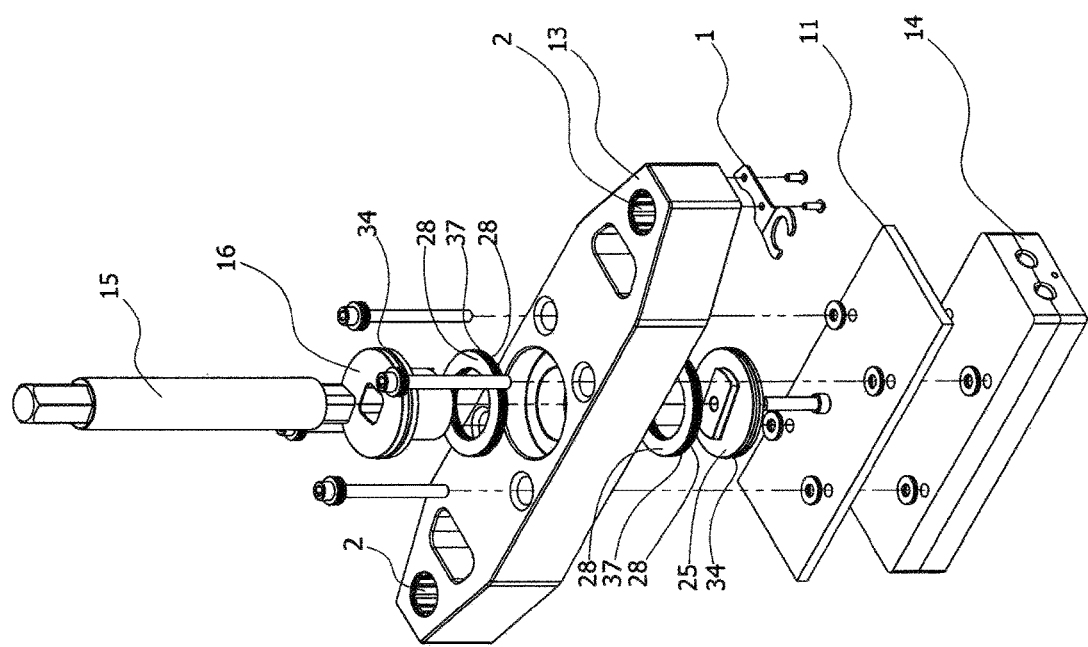
FIG. 6 is an exploded detail view of the screw press.

Referring now to FIG. 6, there is shown an exploded detail view of screw press 100. A lead screw adapter 16 is keyed to a shaft of lead screw 15. Rotary O-ring seals 34 retain food grade grease and are placed above and below upper heat plate truss 13, as are sets of needle thrust washers 28 and bearings 37. A lead screw adapter cap 25 is disposed beneath lower set of needle thrust washers 28. Lead screw adapter cap 25 is also keyed to lead screw adapter 16, which prevents the single assembly screw from backing out when force is removed and ensures upper and lower bearing assemblies move in unison. An axial gap of 0.005" is created between the bearings 37 when lead screw adapter cap 25 is fastened snuggly to lead screw adapter 16. This calculated axial gap allows for no tangible play in the system while retaining almost zero bearing pre-load. Minimizing bearing pre-load results in low friction, high speed travel while raising or lowering upper heat platen 14. A cable gland mount 1 is attached to the lower surface of upper heat plate truss 13.

Referring now to FIG. 7, there is shown a plan cross sectional front detail view of the upper half of screw press 100.

Figure 8:
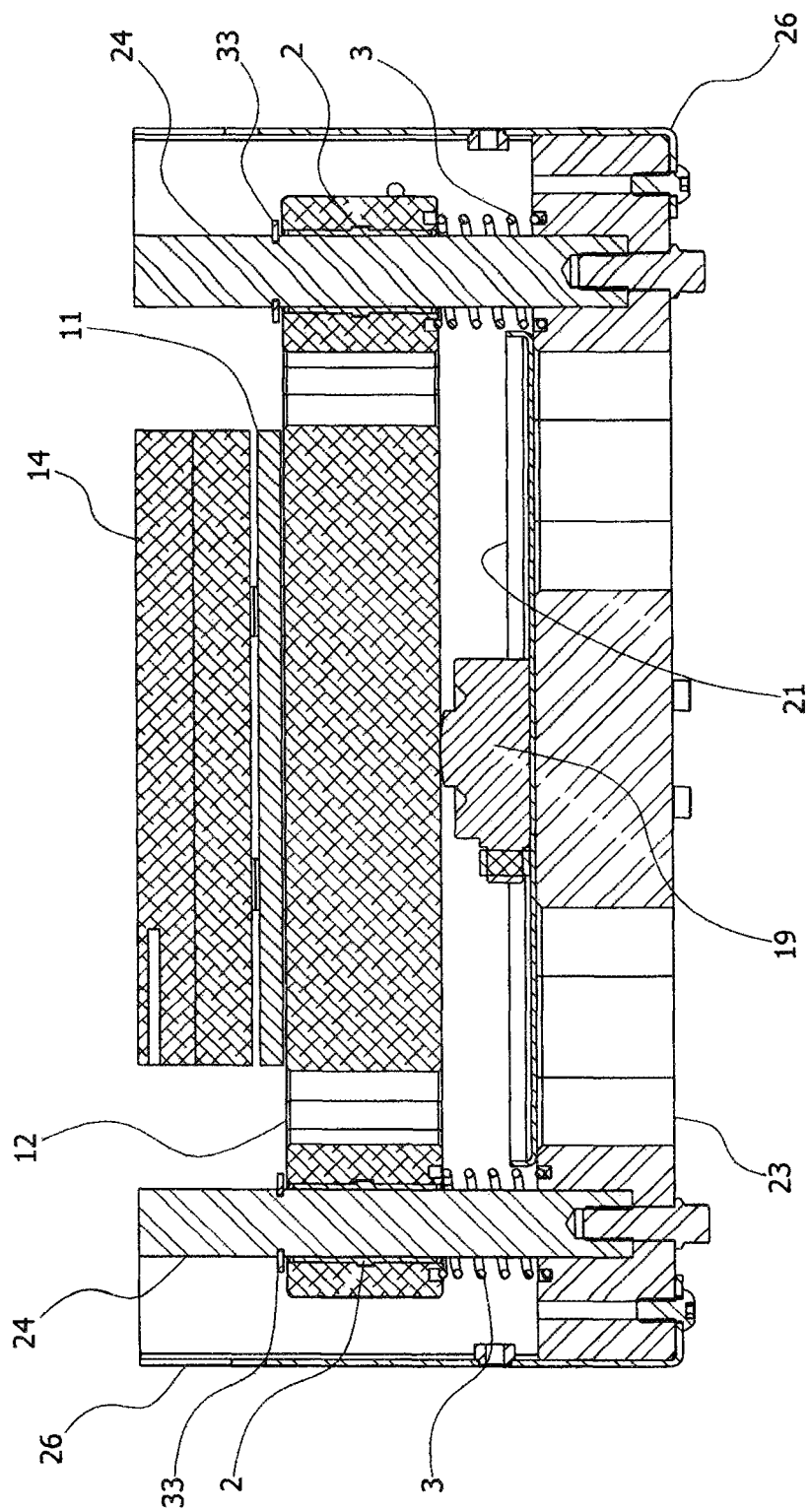
FIG. 8 is a plan cross sectional front detail view of the lower half of the screw press.

Referring now to FIG. 8, there is shown a plan cross sectional front detail view of the lower half of screw press 100.

In operation, the user powers on press 100 and pre-heats heat platens 14 to a desired temperature. Meanwhile, the user places raw material inside a filter bag (not shown) or wrapped with filter cloth. A sheet of precut parchment paper (not shown) is folded in half and the folded edge thereof is tucked into rear parchment clip 29. The raw material/filter bag is placed between the parchment paper and the open ends are tucked into a front parchment clip 29, thus securing the bag from movement while heat platens 14 are engaged.

Once platens 14 are at temperature as indicated on touchscreen display 38, the user may press the start button on touchscreen display 38, which activates the timer and the guided recipe. The user may begin to twist handle 10 clockwise to start applying force. Display 38 shows numerical and graphical information to guide the user to the target force as handle 10 is turned. Oil begins to flow from the material and onto the parchment paper or into collection tray and/or drip pan 32. Fractional separation is possible through a progression of force, time, and temperature. Each of the primary parameters is programmable and can by changed on the fly at any time or a specific recipe may be followed with precision.

When the timer ends or the user determines that the operation is complete, the stop button on touchscreen display 38 is pushed and handle 10 is turned counterclockwise to remove force and retract upper heat platen 14. The parchment paper is set aside to cool for a few minutes and then opened to remove the filter material and collect the oil via a PurePressure scraping tool (not shown). This oil is 100% ready for consumption, with no mandatory need for post-processing or vacuum purging. Additional processing, of course, is possible to obtain a large variety of textures and final products including, but not limited to, oil for vaporizer pens.

Real-time data is collected from every pressing operation and can be saved as a new or revised recipe. The user may tweak the data points and add additional information such as strain name, material type (flower, kief or bubble hash), material weight in grams, filter bag size, filter bag micron rating, and the relative humidity of the initial raw material.

Alternatively, load cell 19 and software display 38 can provide an indication that the extraction process has completed. The press is a positional force application method, so the operator has two options for applying force and achieving the software set point on display 38: (a) by constantly pushing on the handle 10 (i.e., not releasing it), or (b) by pushing on handle 10 and then releasing it. As the oil exits the raw material, the volume of the patty decreases, and the pressure applied on that raw material decreases. By utilizing the method of pushing handle 10 and releasing it, the operator can visibly see the pressure decreasing on display 38. As the extraction process continues, the operator can repeatedly return to the pressure set point until pressure on the patty is no longer decreasing. Once pressure is no long decreasing, the operator knows that all the oil has been extracted from the raw material. His indication that the oil has left the patty can be identified by either software notifications or by the operator observing pressure drop on display 38.

The inventive helix press is an excellent tool for recipe creation because the end of a press cycle can be detected. The obvious benefit of end point detection is the ability to know when most of the oil is completely extracted from the raw material. This ensures the user leave no oil in the raw material, which, in turn, reduces profits.

End point detection is possible through the combination of positional force application and live force measurements via integrated load cell 19. A puck of raw plant material wrapped in filter media, not shown, is placed between the heat plates 14 with a folded piece of parchment paper as a barrier. The user begins to apply a force and the heat begins to liquefy the oils. As the liquid oils are expressed and pressed out of the filtration sock, the puck of raw material is reduced in height.

Since the press 100 utilizes a positional force application (screw drive) for lead screw 15, the user keeps turning handle 10 to hold a constant force as oil is expressed from the filter sock. The user ramps up pressure through a series of stages in the recipe. With each stage, there progressively less oil is extracted with the increased force. At the end of the final stage, the user increases force to hold stable without the need to turn handle 10. This is the indicator that the end point has been reached for the current temperature setting.

It is important to note that an end point is only valid for a specific temperature and batch of raw material. The batch size should be consistent in order to achieve consistent results. The firmware in helix press 100 helps the user determine when the end point has been reached by evaluating the change in force over time. Near the end of a press cycle, the press display 38 instructs to the user to increase the force. The user does so and, when that force is achieved, the firmware instructs the user to then release handle 10 completely.

At this point, the firmware reads data from load cell 19 as displayed on screen display 38 and continuously calculates the change in force over time ($\Delta F/\Delta t$). If ($\Delta F/\Delta t$)≅0.0 lbf/sec, then the end point has been detected. Once a proper recipe has been created, it is saved as a new recipe.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a great number of variations of the devices, device components, and method steps set forth in the present description. As will be obvious to one of skill in the art, methods and devices useful for the present methods can include a great number of optional composition and processing elements and steps.

Whenever a range is given in the specification, for example, a temperature range, all intermediate ranges and subranges, as well as all individual values included in the range given, are intended to be included in the disclosure. It will be understood that any subranges or individual values in a range or subrange that are included in the description herein can be excluded from the claims herein.

All patents mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein, any of the terms "comprising", "consisting essentially of," and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Since other modifications and changes varied to fit particular operating requirements and environments will be apparent to those skilled in the art, the invention is not considered limited to the example chosen for purposes of disclosure and covers all changes and modifications which do not constitute departures from the true spirit and scope of this invention.

Having thus described the invention, what is desired to be protected by Letters Patent is presented in the subsequently appended claims.

What is claimed is:

1. A hand-operated, solventless screw press, comprising:
   a) two oppositely disposed heat plates for generating force to raw material in order to extract oil therefrom, the heat plates are an upper heat plate and a lower heat plate;
   b) a rotatable handle operatively connected to at least one of the two heat plates for adjusting a distance therebetween;
   c) a force measuring digital load cell operatively in contact with at least one of the heat plates;
   d) a display operatively connected to the load cell for displaying pressure being applied by the heat plates in real time;
   e) a structural frame including guide rods surrounding and holding the upper heat plate and the lower heat plate in place, the guide rods resisting rotary forces from the handle and translating force from the handle into linear movement of at least one of the heat plates;
   f) a lead screw disposed between the guide rods and connecting the handle and upper heat plate, wherein the handle is rotatably mounted to a shaft of the lead screw such that rotational movement of the handle is translated into a vertical force on the upper heat plate; and
   g) at least one compression spring disposed below the lower heat plate and configured to apply an upward force to lift the lower heat plate off the load cell.

2. The hand-operated, solventless screw press in accordance with claim 1, wherein the two heat plates are capable of exerting up to approximately 1,000 psi across the material.

3. The hand-operated, solventless screw press in accordance with claim 1, wherein the display comprises a touch screen display.

4. The hand-operated, solventless screw press in accordance with claim 1, wherein the raw material is chosen from a set of materials consisting of: cannabis flower and isolated trichome heads.

5. The hand-operated, solventless screw press in accordance with claim 1, further comprising;
   h) means for measuring and recording a change in force over time.

6. The hand-operated, solventless screw press in accordance with claim 5, wherein an end point of a process for extracting oil from the raw material is detected when the change in force is approximately 0.0 lbf/sec.

7. The hand-operated, solventless screw press in accordance with claim 1, further comprising:
   h) means for creating and storing a recipe representative of at least one of a set parameters consisting of: heat plate temperature; time of operation; pressure ramping; capacity of the press; type of raw material; and mass of raw material.

8. The hand-operated, solventless screw press in accordance with claim 7, further comprising:
   i) means for scaling the recipe in size based upon at least one of the set of parameters.

9. The hand-operated, solventless screw press in accordance with claim 7, wherein the recipe can be used on any suitable rosin press machine.

10. The hand-operated, solventless screw press in accordance with claim 1, wherein the load cell acts as a center contact point for the lower heat plate.

11. The hand-operated, solventless screw press in accordance with claim 1, wherein the lead screw connects to the upper heat plate at a central location of the upper heat plate, and centrally between the guide rods.

12. The hand-operated, solventless screw press in accordance with claim 11, wherein the guide rods are configured to hold the upper heat plate and the lower heat plate while allowing linear movement of both the upper heat plate and the lower heat plate in a vertical direction.

13. The hand-operated, solventless screw press in accordance with claim 1, wherein the at least one compression spring includes a plurality of compression springs, each of the compression springs is disposed around the respective guide rod.

14. The hand-operated, solventless screw press in accordance with claim 13, further comprising:
   h) retaining rings surrounding the guide rods, the retaining rings preventing movement of a lower heat plate truss of the lower heat plate beyond the retaining rings, wherein when no downward force is applied to the lower heat plate, the compression springs lift the lower heat plate truss against the retaining rings.

* * * * *